(12) United States Patent
Kolster

(10) Patent No.: US 7,582,105 B2
(45) Date of Patent: *Sep. 1, 2009

(54) SUTURE FOR WOUND CLOSURE, TISSUE APPROXIMATION, TISSUE SUPPORT, SUSPENSION AND/OR FIXATION

(75) Inventor: Alwin Kolster, Corona, CA (US)

(73) Assignee: Silhouette Lift Societad Limitada, Barcelona (ES)

( * ) Notice: Subject to any disclaimer, the term of this patent is extended or adjusted under 35 U.S.C. 154(b) by 72 days.

This patent is subject to a terminal disclaimer.

(21) Appl. No.: 11/500,733

(22) Filed: Aug. 7, 2006

(65) Prior Publication Data

US 2007/0038249 A1 Feb. 15, 2007

Related U.S. Application Data

(63) Continuation-in-part of application No. 11/168,173, filed on Jun. 28, 2005, now Pat. No. 7,468,068.

(60) Provisional application No. 60/584,927, filed on Jun. 30, 2004.

(51) Int. Cl.
    *A61B 17/04* (2006.01)
(52) U.S. Cl. ...................... 606/228; 606/232
(58) Field of Classification Search ......... 606/228–232, 606/220
    See application file for complete search history.

(56) References Cited

U.S. PATENT DOCUMENTS

| 4,750,492 | A | * | 6/1988 | Jacobs | 606/230 |
|---|---|---|---|---|---|
| 5,269,783 | A | * | 12/1993 | Sander | 606/148 |
| 5,269,809 | A | * | 12/1993 | Hayhurst et al. | 606/232 |
| 5,330,503 | A | * | 7/1994 | Yoon | 606/223 |
| 5,350,399 | A | * | 9/1994 | Erlebacher et al. | 606/213 |
| 5,374,268 | A | * | 12/1994 | Sander | 606/148 |
| 5,584,859 | A | * | 12/1996 | Brotz | 606/228 |
| 5,984,933 | A | * | 11/1999 | Yoon | 606/148 |
| 6,086,608 | A | * | 7/2000 | Ek et al. | 606/232 |
| 6,102,947 | A | * | 8/2000 | Gordon | 623/13.11 |
| 6,280,474 | B1 | * | 8/2001 | Cassidy et al. | 623/16.11 |
| 6,511,498 | B1 | * | 1/2003 | Fumex | 606/232 |
| 6,585,730 | B1 | * | 7/2003 | Foerster | 606/32 |
| 7,090,690 | B2 | * | 8/2006 | Foerster et al. | 606/232 |
| 7,128,753 | B1 | * | 10/2006 | Bonutti et al. | 606/232 |
| 7,468,068 | B2 | * | 12/2008 | Kolster | 606/228 |
| 2003/0149447 | A1 | * | 8/2003 | Morency et al. | 606/228 |
| 2004/0138683 | A1 | * | 7/2004 | Shelton et al. | 606/151 |
| 2004/0138704 | A1 | * | 7/2004 | Gambale et al. | 606/213 |
| 2007/0219587 | A1 | * | 9/2007 | Accardo | 606/228 |

\* cited by examiner

*Primary Examiner*—Darwin P Erezo
(74) *Attorney, Agent, or Firm*—Willie Krawitz

(57) ABSTRACT

A suture assembly includes an elongated flexible body which may be either a single filament for a multiple strand braided or woven body, supporting a plurality of shaped tissue-engaging elements in a generally spaced arrangement thereon. A curved body having a sharp point is joined to one end of the flexible body while a straight pointed body is joined to the remaining end of the flexible body. In alternate embodiments, the tissue-engaging elements define a variety of cross-section shapes. In a further alternate embodiment, the tissue-engaging elements are divided into first and second oppositely facing sets to provide a bidirectional suture. In a still further alternate embodiment, the elongated flexible body supports an elongated tissue-bonding sleeve.

13 Claims, 9 Drawing Sheets

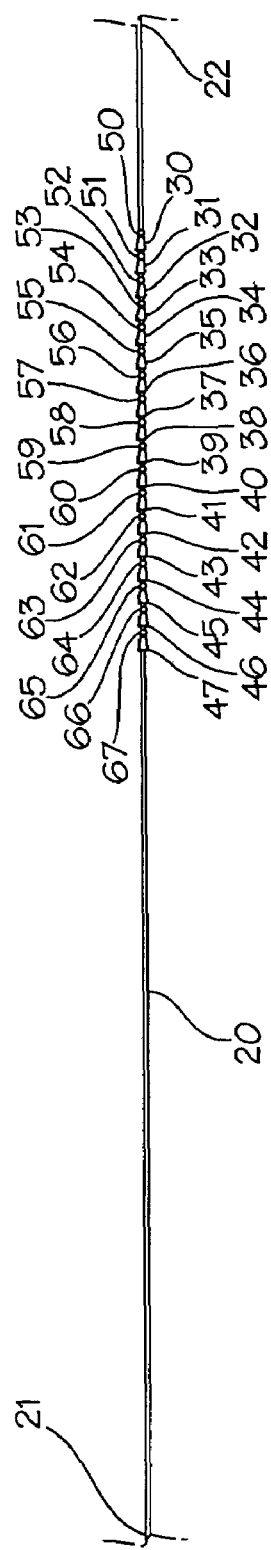
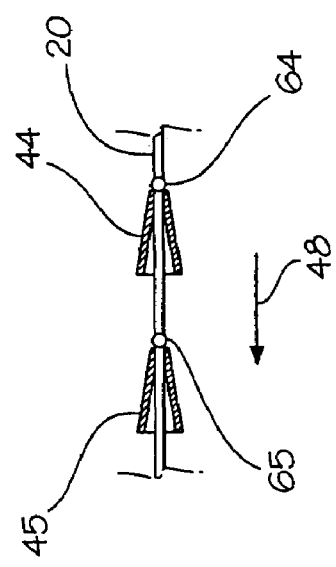
FIG. 2
FIG. 3

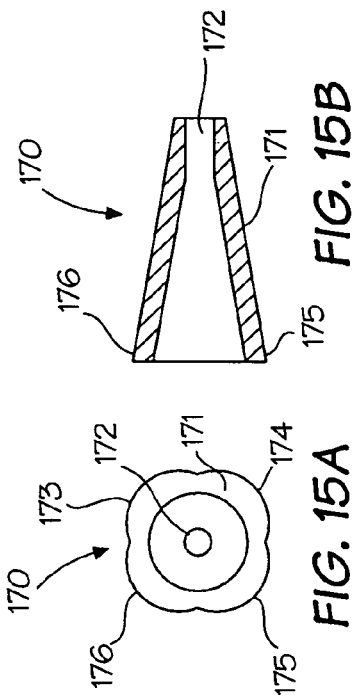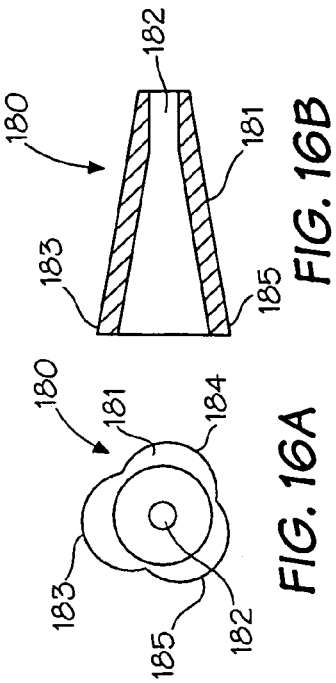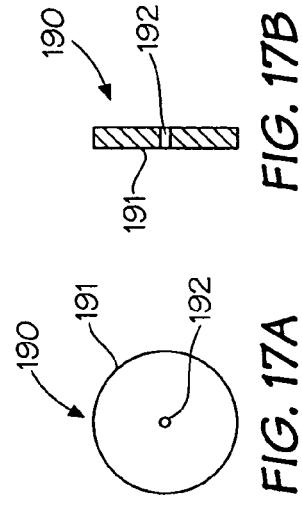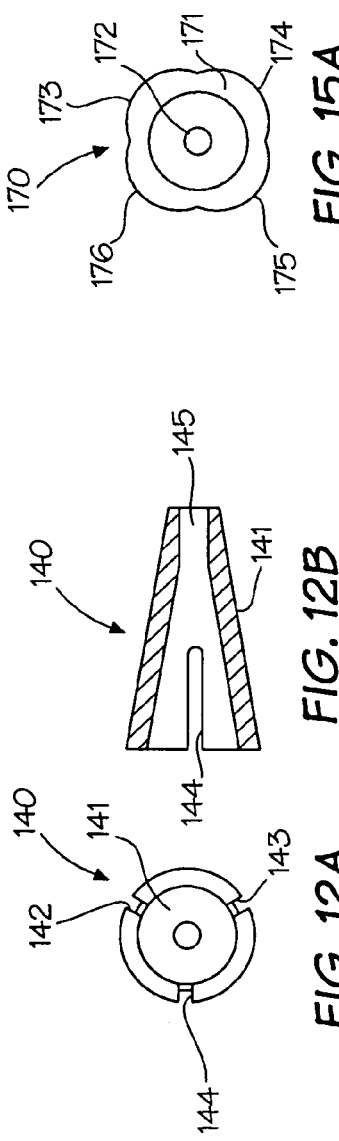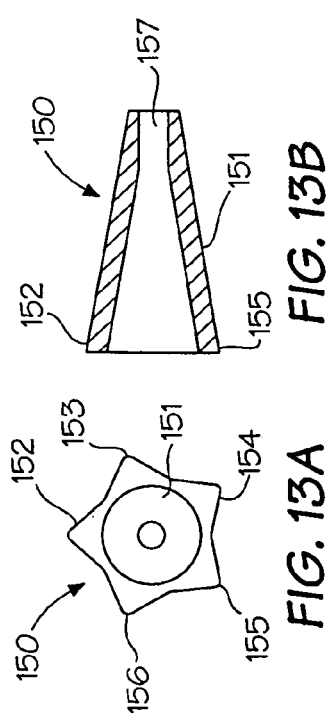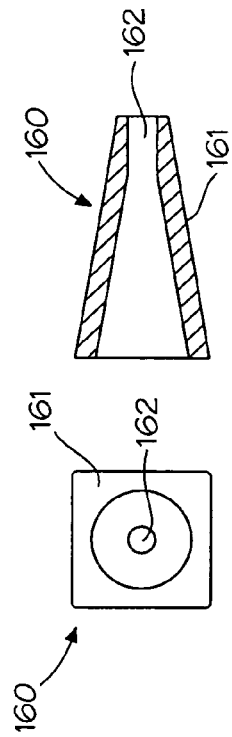

SUTURE FOR WOUND CLOSURE, TISSUE APPROXIMATION, TISSUE SUPPORT, SUSPENSION AND/OR FIXATION

CROSS-REFERENCE TO RELATED APPLICATIONS

This application is a continuation-in-part of U.S. patent application Ser. No. 11/168,173, filed Jun. 28, 2005, now U.S. Pat. No. 7,468,068, on behalf of the present applicant and which is entitled SUTURE FOR WOUND CLOSURE, TISSUE APPROXIMATION, TISSUE SUPPORT, SUSPENSION AND/OR FIXATION which is herby incorporated herein by reference and which in turn claims the benefit of and priority under 35 U.S.C. 119(e) of U.S. Provisional Patent Application No. 60/584,927 filed Jun. 30, 2004 as incorporated herein by reference.

FIELD OF THE INVENTION

This invention relates generally to apparatus for tissue suturing and particularly to apparatus for surgical incision or wound closure as well as tissue approximation in surgical procedures such as cosmetic surgery.

BACKGROUND OF THE INVENTION

A substantial number of devices have been provided throughout the years which may be used for closure of a wound or surgical incision. Such devices have included staples, sewing and stitching as well as tissue connecting sutures.

One recently developed type of suture maybe generally described as a "barbed suture". Such sutures generally comprise elongated thin filaments having pluralities of tissue-engaging barbs and are designed for closure of wounds or surgical incisions. In such use, the main filament applies drawing tension while the pluralities of tissue-engaging barbs increase the "grip" of the suture to the drawn tissue.

Not surprisingly, the need for ever-improved sutures has prompted practitioners in the art to provide a variety of suture structures which can be generally described as barbed sutures. For example, U.S. Pat. No. 3,123,077 issued to Alcamo sets forth a SURGICAL SUTURE having an elongated flexible filament defining a plurality of outwardly extending barbs or projections formed on its surface.

U.S. Pat. No. 6,241,747 issued to Ruff sets forth a BARBED BODILY TISSUE CONNECTOR having an elongated filament or body which supports a plurality of closely spaced barbs disposed along the body. The barbs are pointed in a first direction on one portion of the body and in an opposite direction on the remaining portion of the body.

U.S. Pat. No. 5,425,747 issued to Brotz sets forth a SUTURE formed of a bioabsorbable material having a central body defining a plurality of lateral members extending perpendicularly therefrom in the same general plane with the central body. Each lateral member further defines a plurality of barb members extending at acute angles therefrom. The lateral members are constructed to be inserted laterally into two sides of a tissue cut and to provide a securely retained structure.

U.S. Pat. No. 5,584,859 issued to Brotz sets forth a SUTURE ASSEMBLY formed of a bioabsorbable material having a central body member and a plurality of elongated members in a plane extending perpendicularly on each side therefrom. The extending lateral members are interconnected to the central body member by connectors and each support a plurality of acutely angled barb members extending from their respective outer surfaces.

While the foregoing described prior art devices have to some extent improved the art and in some instances enjoyed commercial success, there remains nonetheless a continuing need in the art for evermore improved tissue sutures.

SUMMARY OF THE INVENTION

Accordingly, it is a general object of the present invention to provide an improved apparatus for tissue suturing. It is a more particular object of the present invention to provide an improved apparatus for wound closure, tissue approximation, tissue support, suspension and/or fixation. It is a still more particular object of the present invention to provide an improved suture apparatus which is particularly advantageous in cosmetic surgery procedures directed toward recently emerging nonsurgical minimally invasive cosmetic surgery procedures directed toward facial lifting and contouring.

Thus, the inventive suture structure of the present invention provides an implantable directional camming device which may be fabricated in either a directional or bi-directional structure. The suture apparatus of the present invention may be formed of elements which are injection molded or cold-headed and maybe used for wound closure, tissue approximation, tissue support, suspension and/or fixation. The molded or cold-headed elements may be formed having any of a number of cross-sections as desired. The suture of the present invention is constructed to be implanted into the human body with or without the use of an introducer and is designed to work in conjunction with the healing process post surgical such as scar tissue formation and fibrosis. The inventive suture apparatus holds wounds closed or fixates tissue without the need for suture knot tying to maintain tissue approximation. The inventive structure being formed of injection molded or cold-headed elements may be formed without the need for conventional machine cutting to provide tissue-gripping structure.

In certain embodiments of the present invention, the suture may be formed of a braided polyester, nylon or the like. In further embodiments, the suture may further include an elongated porous sleeve to aid in tissue-bonding.

Thus, in accordance with the present invention, there is provided a suture comprising: an elongated flexible body having first and second ends; a plurality of tissue-engaging elements each defining a bore therethrough, the tissue-engaging elements received upon the elongated flexible body; and a plurality of knots tied in the elongated flexible body each larger than the bore, the knots maintaining the tissue-engaging elements in a serial arrangement on the elongated flexible body; and an elongated porous tissue bonding sleeve supported upon said elongated flexible body.

In further accordance with the present invention, there is provided a suture assembly comprising: an elongated needle body having a first pointed end and a first connector end; a curved needle body having a second pointed end and a second connector end; an elongated filament having a first end joined to the first connector end, a second end joined to the second connector end, and a plurality of knots formed in the filament; a plurality of tissue-engaging elements each defining a bore therethrough, the tissue-engaging elements being received upon the filament by passing the filament through the bores with each tissue-engaging element being proximate one of the knots; and an elongated porous tissue bonding sleeve supported upon the elongated flexible body.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 2 sets forth a side view of the suture portion of the present invention suture assembly;

FIG. 3 sets forth a section view of an illustrative segment of the tissue-gripping portion of the present invention suture;

FIGS. 12A and 12B set forth respective front and section views of a tissue-gripping element constructed in accordance with the present invention having a generally conical shape and slot configuration;

FIGS. 13A and 13B set forth respective front and section views of a tissue-gripping element defining a generally five-sided tapered shape;

FIGS. 14A and 14B set forth respective front and section views of a tissue-gripping element defining a generally square cross-section;

FIGS. 15A and 15B set forth respective front and section views of a tissue-gripping element defining a four lobed cross-section;

FIGS. 16A and 16B set forth respective front and section views of a tissue-gripping element defining a three lobed cross-section;

FIGS. 17A and 17B set forth respective front and section views of a flat disc-like tissue-gripping element;

DESCRIPTION OF THE PREFERRED EMBODIMENTS OF THE INVENTION

Figure 1:
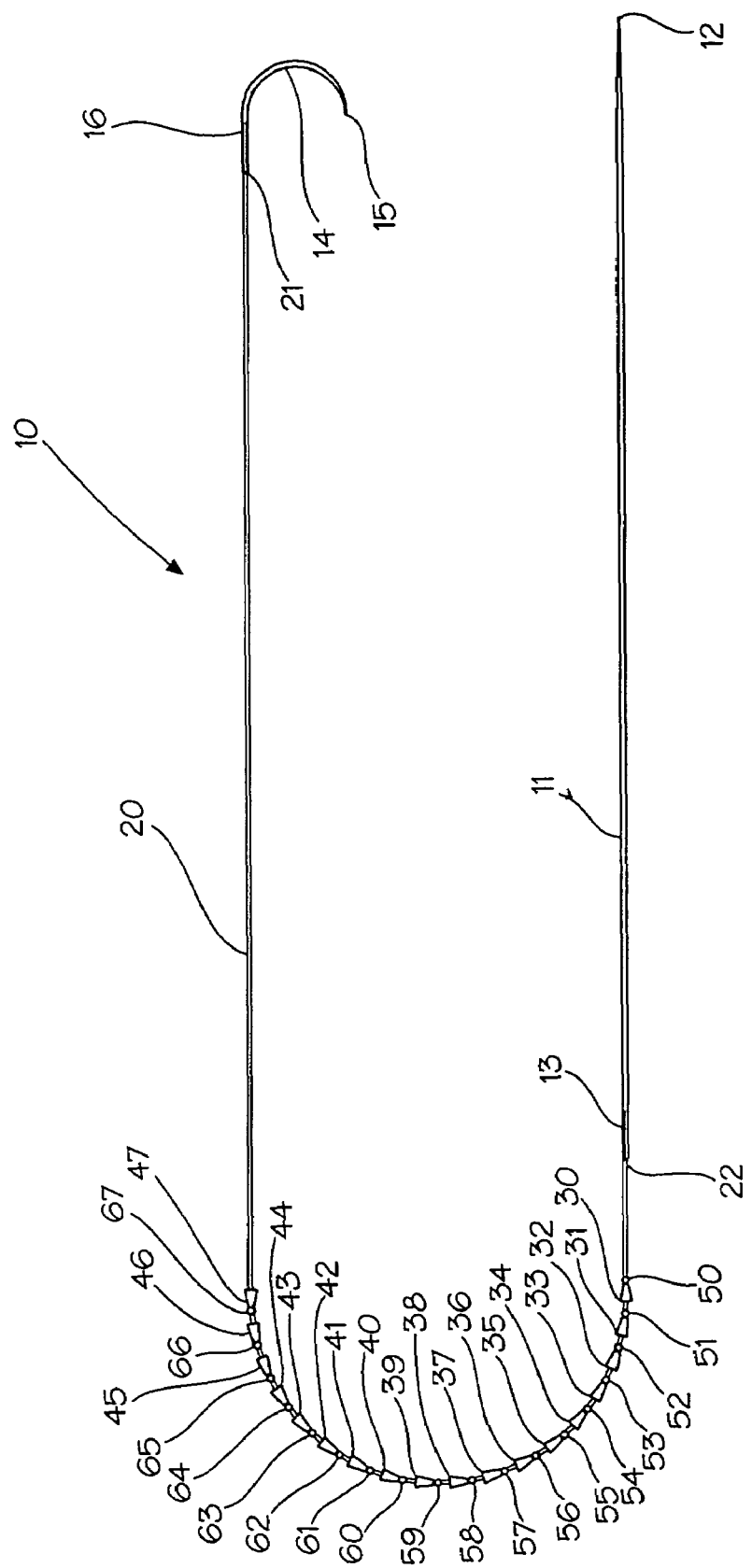
FIG. 1 sets forth a side view of a complete suture assembly constructed in accordance with the present invention.

FIG. 1 sets forth a side view of a suture assembly constructed in accordance with the present invention and generally referenced by numeral 10. By way of overview, suture assembly 10 comprises four basic elements which are a generally straight body 11, a flexible elongated body 20, a plurality of tissue-engaging elements 30 through 47 and a curved body 14. More specifically, suture assembly 10 includes an elongated straight body 11 formed of a plastic material such as polypropylene or the like and includes a generally pointed end 12 and a connector end 13. Suture assembly 10 further includes a flexible elongated filament body 20 having an end 22 secured to connector 13 in the manner described below. Flexible body 20 further supports a plurality of tissue-engaging elements 30 through 47 set forth below in greater detail ill FIGS. 4 and 5. Suffice it to note here that tissue-engaging elements 30 through 47 are substantially identical in structure and are received upon flexible body 20. In addition, tissue-engaging elements 30 through 47 comprise generally conical structures which impart a directional character to the suture assembly in its engagement of tissue. As is better seen in FIG. 3, flexible body 20 further defines a plurality of tied knots 50 through 67 which are tied within flexible body 20 to provide limitation of the movement of tissue-engaging elements 30 through 47 upon flexible body 20. Flexible body 20 further defines an end 21 which is received within a connector 16 of curved body 14. Curved body 14 further defines a sharp pointed end 15. Connectors 13 and 16 secure ends 22 and 21 of flexible body 20 by use of a conventional crimping attachment. The present invention suture may be fabricated of either absorbative or non-absorbative materials to suit the patient and the procedure.

As mentioned above, the present invention suture assembly is suitable for use in a variety of wound closure, tissue approximation, tissue support, suspension and/or fixation procedures. However, as is also mentioned above, the present invention suture assembly is particularly well suited to use in procedures which involve face-lifting or contouring during cosmetic surgery procedures. During such use, the directional grip or directional character provided by tissue-engaging elements 30 through 47 further enhance the lifting and contouring capability of the suture. In its preferred fabrication, the entire suture is formed of a monofilament material such as polypropylene or the like. Alternatively, an absorbable material such as PDF may be used. Once inserted under the skin, the directional character of tissue-engaging elements 30 through 47 form a permanent support structure for the tissue and actually lift and contour the tissue. While not limited to use in any particular procedure, the present invention suture is well suited to use for lifting and contouring nasolabral lines (smile lines) as well as retracting of the patient's jowls or other parts of the body which need lifting or contouring. The procedure utilizing the present invention suture is extremely safe and requires relatively little time compared to conventional cosmetic surgery. The procedure utilizing the present invention suture may be performed under local anesthesia with the patient remaining comfortably awake. During the procedure, the suture is inserted deep into the subcutaneous tissue along the lines where the new contour is desired. Typically, as few as three suture insertions significantly raise the cheek contour while as few as two sutures correctly placed may be utilized to draw back the patient's jowls. The suture may also be used to raise the patient's brow and pull back neck tissue. Also, the present invention suture may be used elsewhere such as pulling in waist lines. Once inserted, the gripping power and lifting effect of the tissue is maximized after several months when the collagen of the patient's tissue has formed around the tissue-engaging elements.

It will be apparent to those skilled in the art that the number of tissue-engaging elements utilized in the present invention suture assembly is to some extent a matter of choice and may readily be varied for suitability to specific applications or uses. Thus, the number of tissue-engaging elements shown in FIG. 1 should be regarded as illustrative of the principles of operation of the present invention suture assembly and not as limitation as to the inventive structure.

FIG. 2 sets forth a side view of the suture portion of suture assembly 10. As described above, the present invention suture includes an elongated flexible preferably monofilament body 20 formed of a material such as polypropylene or the like. Flexible body 20 defines an end 21 and an end 22. A plurality of tissue-engaging elements 30 through 47 are threaded upon flexible body 20. As is better seen below in FIG. 3, flexible body 10 is tied to define a plurality of knots (knots 50 through 67 shown in FIG. 1). Knots 50 through 67 are positioned upon flexible body 20 at generally evenly spaced intervals and are utilized in limiting the movement of tissue-engaging elements 30 through 47 upon flexible body 20. Thus, it will be apparent that tissue engaging elements 30 through 67 are serially placed upon flexible body 20 and that a corresponding plurality of knots 50 through 67 are tied in front of each tissue-engaging element as it is threaded upon end 22 of flexible body 20. For example, assembly of tissue-engaging elements 30 through 47 upon flexible body 20 is initiated by threaded tissue-engaging element 47 passed end 22 to the desired position on body 20. Thereafter, knot 67 is tied in flexible body 20. Next, tissue engaging element 67 is threaded upon end 22 of flexible body 20 and positioned in proximity to tissue engaging element 47. Thereafter, flexible body 22 is tied to form knot 66. This procedure continues as each tissue-engaging element is threaded upon end 22 of flexible body 20 and thereafter moved into proximity of the preceding tissue-engaging element after which the corresponding positioning knot is tied in flexible body 20—Once all of the desired tissue-engaging elements have been assembled to flexible body 20 and the corresponding travel limiting knots have been tied within flexible body 20, flexible body 20 is ready for assembly to straight body portion 11 and curved body portion 14 (seen in FIG. 1) to complete the suture.

FIG. 3 sets forth an enlarged view of a portion of flexible body 20 having section views of tissue-engaging elements 44 and 45 secured thereon in the manner described above. Thus, in the example of FIG. 3, flexible body 20 is shown supporting tissue engaging elements 44 and 45. Correspondingly, flexible body 20 has been tied to form a pair of knots 65 and 64 each of which limit the positions of corresponding of tissue-engaging elements 44 and 45. In this manner, tissue-engaging elements 44 and 45 are able to transfer drawing force from flexible body 20 to surrounding tissue which is engaged by elements 44 and 45. Once again, it will be noted that this engagement is directional in that elements 44 and 45 provide substantial greater engagement of tissue in the direction indicated by arrow 48.

Figure 4:
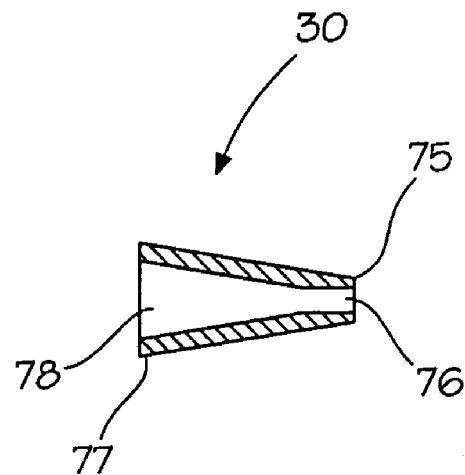
FIG. 4 sets forth a section view of a tissue-gripping element prior to installation in the suture assembly.

FIG. 4 sets forth a section view of tissue-engaging element 30. It will be apparent to those skilled in the art that tissue-engaging elements 30 through 47 (seen in FIG. 1) are substantially identical in construction. Thus, FIG. 4 and the descriptions which are provided in conjunction therewith will be understood to apply equally well to tissue-engaging elements 31 through 47. More specifically, tissue-engaging element 30 is generally frusto-conical in shape and thus defines a narrow end 75 and a flared end 77. End 75 defines a bore 76 which is sized to fit snugly upon flexible body 20 (seen in FIG. 2). Flared end 77 provides increased volume for interior portion 78 thereof. The conical shape of tissue-engaging element 30 together with the open character of flared end 77 and interior 78 cooperate to provide a substantial tissue-engaging property for element 30. As mentioned above, the tissue-engaging elements of the present invention maybe fabricated using injection molding or cold-heading techniques as desired. While a number of suitable materials may be utilized in fabricating the tissue engaging elements of the present invention suture assembly, materials such as polypropylene or the like have been found to be suitable and advantageous. Alternatively, absorbable materials may also be used.

Figure 5:
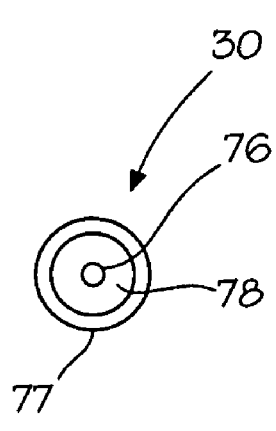
FIG. 5 sets forth a front view of the tissue-gripping element of FIG. 4.

FIG. 5 sets forth a rear view of tissue-engaging element 30 showing flared end 77 and interior 78. Also seen in FIG. 5 is the extension of bore 76 through end 75 of the tissue-engaging element.

Figure 6:
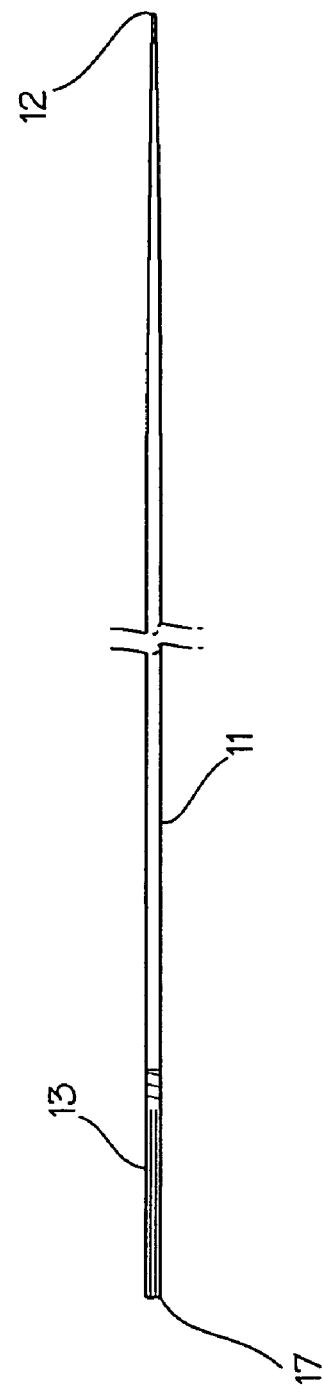
FIG. 6 sets forth a side view of the straight needle portion of the present invention suture assembly.

FIG. 6 sets forth a partially sectioned side view of straight body 11 in the absence of attachment to flexible body 20. As is described above, straight body II is fabricated of a suitable material such as polypropylene or the like and defines a tapered end 12 forming a somewhat pointed end structure together with a connector end 13. Connector end 13 is shown in partial section and defines an internal bore 17. Bore 17 is sized to receive the end portion of flexible body 20 (seen ill FIG. 1). Connector 13 secures straight body 11 to flexible body 20 through the application of a conventional crimping process once the end portion of flexible body 20 has been received within bore 17.

Figure 7:
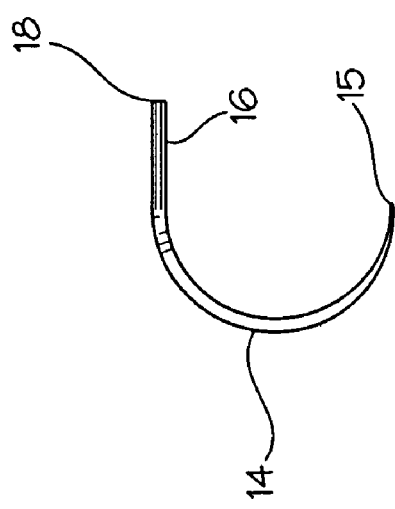
FIG. 7 sets forth a side view of the curved needle portion of the present invention suture assembly.

FIG. 7 sets forth a partially sectioned view of curved body 14. As described above, curved body 14 defines a sharp pointed end 15 and a connector end 16. Connector end 16 defines an internal bore 18 which is sized to receive the end portion of flexible body 20 (seen in FIG. 1) in a snug-fit. Curved body 14 is preferably formed of a plastic material such as polypropylene or the like. The attachment of connector end 16 to flexible body 20 to form the structure shown above in FIG. 1 is carried forward by inserting end 21 of flexible body 20 (seen in FIG. 1) into bore 18 after which a conventional crimping operation is applied to connector end 16. The very sharp point formed in end 15 facilitates the insertion of curved body 14 into skin or other tissue.

Figure 9:
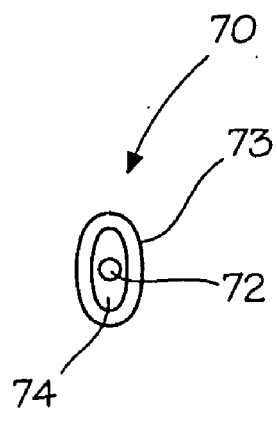
FIG. 9 sets forth a front view of the tissue-gripping element of FIG. 8.
Figure 8:
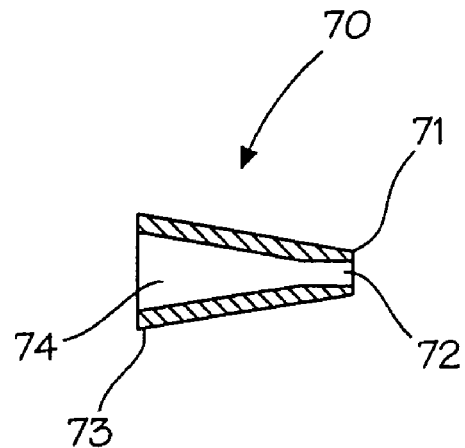
FIG. 8 sets forth a section view of an alternate embodiment tissue-gripping element.

FIGS. 8 and 9 set forth respective section and rear views of an illustrative alternate embodiment tissue-engaging element. The difference between the tissue-engaging element illustrated in FIGS. 8 and 9 and the tissue-engaging element set forth in FIGS. 4 and 5 is found in the generally elliptical cross-sectional shape rather than the circular cross-section shape found in the above-described embodiments.

More specifically, FIG. 8 sets forth a section view of an elliptically shaped tissue-engaging element generally referenced by numeral 70. Tissue engaging element 70 defines a narrow end 71 having a bore 72 formed therein. Element 70 further defines a flared end 73 and an interior 74. Element 70 is preferably fabricated utilizing injection molding or cold-heading manufacturing processes. It will be apparent to those skilled in the art that tissue-engaging element 70 provides a direct alternative replacement to tissue-engaging elements 30 through 47 shown in FIG. 1. It will be further apparent to those skilled in the art that a plurality of tissue-engaging elements such as element 70 may be utilized in the same manner as elements 30 through 47 described above. In certain applications it has been found that the elliptical cross-section of tissue-engaging element 70 provides some advantage; however, in general, the operation of tissue-engaging element 70 is substantially identical to the operation of tissue-engaging element 30 seen in FIG. 4.

FIG. 9 sets forth a rear view of tissue-engaging element 70 showing bore 72 and interior 74 formed therein. Tissue-engaging element 70 further defines a flared end 73.

Figure 10:
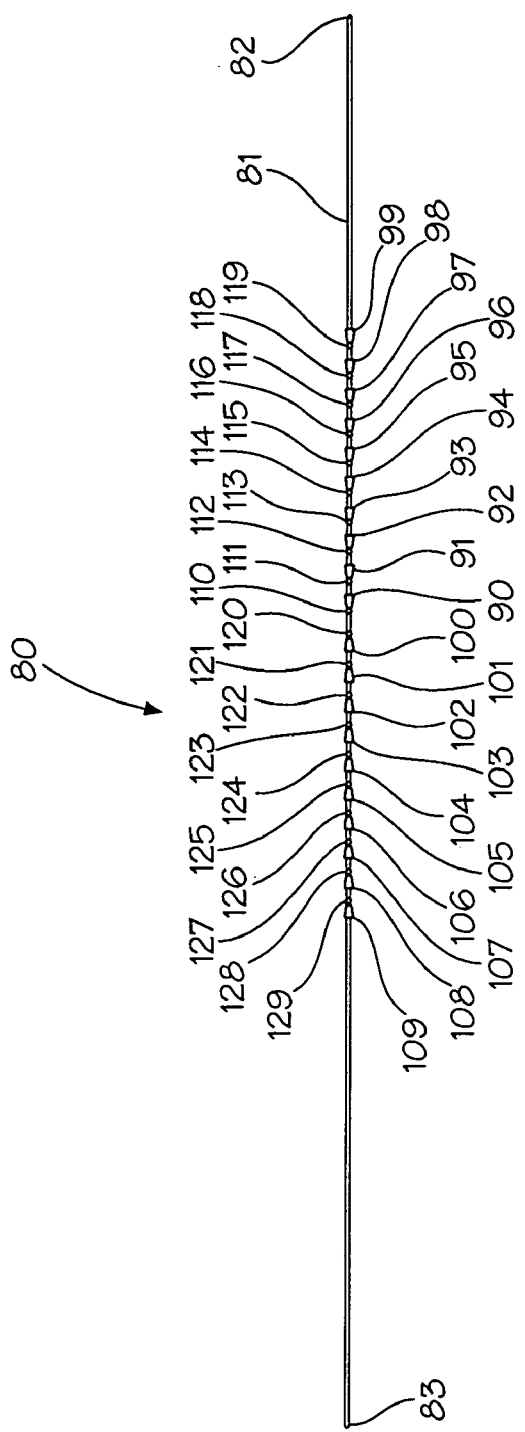
FIG. 10 sets forth a still further alternate embodiment of the present invention which provides a bidirectional suture.

FIG. 10 sets forth a side view of a still further alternate embodiment of the present invention suture generally referenced by numeral 80. It will be apparent to those skilled in the art from a comparison of the embodiment of the present invention shown in FIG. 2 and that which is shown in FIG. 10 that suture 80 provides a bidirectional suture. Suture 80 includes an elongated flexible body 81 having ends 82 and 83. A first plurality of tissue-engaging elements 90 through 99 are supported upon body 81 and are positioned by a plurality of knots 110 through 119. Knots 110 through 119 are tied as simple knots in filamentary body 81 in the manner described above. Suture 80 further includes a second plurality of oppositely facing tissue-engaging elements 100 through 109. Tissue-engaging elements 100 through 109 are positioned upon body 81 in an opposite orientation to that of elements 90 through 99. In a similar fashion to the above-described suture, a plurality of knots 120 through 129 are tied within body 81 to secure the positions of tissue-engaging elements 100 through 109. It will be apparent to those skilled in the art that the opposite orientation of tissue-engaging elements 90 through 99 from tissue-engaging elements 100 through 109 provides suture 80 with a bidirectional gripping characteristic suitable for insertion in surgical procedures where a bidirectional grip is required. It will be equally apparent to those skilled in the art from examining FIGS. 2 and 10 that alternative arrangements to the arrangements of tissue-engaging elements shown in FIGS. 2 and 10 may be utilized without departing from the spirit and scope of the present invention. In accordance with an important advantage of the present invention suture, the position of tissue-engaging elements upon the filamentary body as well as the orientation of the tissue-engaging elements may be varied or combined as desired to meet specific and particular needs in a given procedure.

Figure 11:
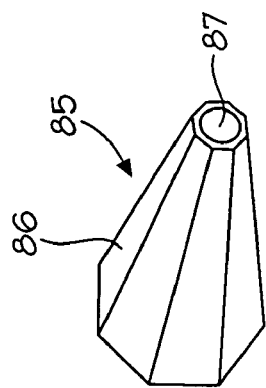
FIG. 11 sets forth a perspective view of a still further alternate embodiment of the present invention.

FIG. 11 sets forth a perspective view of a tissue-engaging element constructed in accordance with a still further alternate embodiment of the present invention. It will be recalled that FIGS. 4 and 5 above set forth a frusto-conical embodiment of the present invention tissue-engaging elements while FIGS. 8 and 9 set forth an elliptically cross-sectioned conical body forming an alternate construction for the tissue-engaging elements. FIG. 11 shows a faceted embodiment of the present invention in which the outer shape of the tapered tissue-engaging element defines a plurality of facets. Thus in FIG. 11, a tissue-engaging element 85 defines a bore 87 therethrough. Tissue-engaging element 85 is generally tapered to define a narrow end and a broader end and is covered on its outer surface by a plurality of facets 86. Tissue engaging element 85 is suitable for substitution in any of the above-described suture assemblies and is representative of a still further alternate shape for the tissue-engaging elements of the present invention suture. Thus, it will be apparent to those skilled in the art that a variety of tissue-engaging element structures or shapes may be envisioned and utilized without departing from the spirit and scope of the present invention.

With concurrent reference to FIGS. 12A and 12B which set forth respective front and section views, a tissue-gripping element 140 defines a frusto-conical body 141 having a front aperture 145 formed therein. Body 141 further defines a plurality of elongated slots 142, 143 and 144. Slots 142, 143 and 144 further aide in the tissue bonding or tissue engagement of tissue engaging element 140.

With concurrent reference to FIGS. 13A and 13B which set forth respective front and section views, a tissue engaging element 150 defines a tapered body 151 having an aperture 157 formed therein. Body 151 further defines a plurality of end lobes 152, 153, 154, 155 and 156. Lobes 152 through 156 cooperate to enhance the tissue bonding and tissue engaging capability of tissue engaging element 150.

With concurrent reference to FIGS. 14A and 14B which set forth respective front and section views, a tissue engaging element 160 includes a tapered body 161 defining an aperture 162 therein. Body 161 defines a generally square-shaped end portion which provides corner sections to enhance the tissue-gripping and tissue engaging capability of tissue engaging element 160.

With concurrent reference to FIGS. 15A and 15B which set forth respective front and section views, a tissue engaging element 170 defines a tapered body 171 having an aperture 172 formed therein. Body 171 further defines a plurality of lobes 173, 174, 175 and 176 at the larger end thereof. Lobes 173 through 176 enhance the tissue engaging and tissue-gripping capability of tissue engaging element 170.

With concurrent reference to FIGS. 16A and 16B which set forth respective front and section views, a tissue engaging element 180 includes a tapered body 181 defining an aperture 182 therein. The enlarged end of body 181 defines a trio of lobes 183, 184 and 185. Lobes 183 through 185 enhance the tissue engaging and tissue-gripping capabilities of tissue engaging element 180.

With concurrent reference to FIGS. 17A and 17B which set forth respective front and section views, a tissue engaging element 190 defines a generally circular disc-shaped body 191 having a center aperture 192 formed therein.

With respect to the variously shaped tissue engaging elements set forth above, it will be apparent to those skilled in the art that a variety of tissue engaging element shapes may be utilized without departing from the spirit and scope of the present invention. It will be equally apparent from the discussions and Figures that follow that a corresponding variety of positioning elements may be utilized to cooperate with the various tissue engaging elements described therein. The essential function of the tissue engaging element is to provide a grip or engaging characteristic for the suture while the function of the positioning elements such as the tied knots set forth above is to provide a restricted movement of the tissue engaging elements and thereby transfer the gripping force between the tissue and the tissue engaging element to the suture body.

Figure 18:
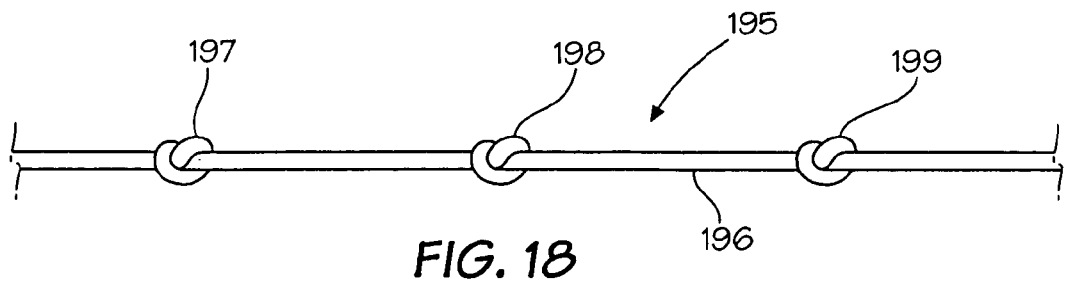
FIG. 18 sets forth a side view of a suture portion constructed in accordance with the present invention and utilizing a plurality of tied knots for tissue-gripping elements.

FIG. 18 sets forth a suture portion which includes tissue gripping elements formed by knots tied in the elongated flexible body of the suture. It will be apparent to those skilled in the art that FIG. 18 shows a portion of a suture constructed in accordance with the present invention. With reference to FIG. 1, it will be recalled that the complete suture structure includes a flexible elongated body together with elongated straight or curved needle portions. Thus, it will be understood that the embodiment shown in FIG. 18 forms a portion of the inventive suture utilizing the remainder of the structure set forth above. More specifically, FIG. 18 shows a portion of a suture 195 having an elongated flexible body 196 which supports a plurality of tissue engaging elements 197, 198 and 199 which are fabricated as knots tied in elongated flexible body 196. It will be apparent to those skilled in the art that the purpose of tying knots such as knots 197, 198 and 199 in body 196 is to provide an enlarged segment which functions as a tissue engaging element. Thus, a variety of different knots may be tied in flexible body 196 to provide this function without departing from the spirit an scope of the present invention.

Figure 19:
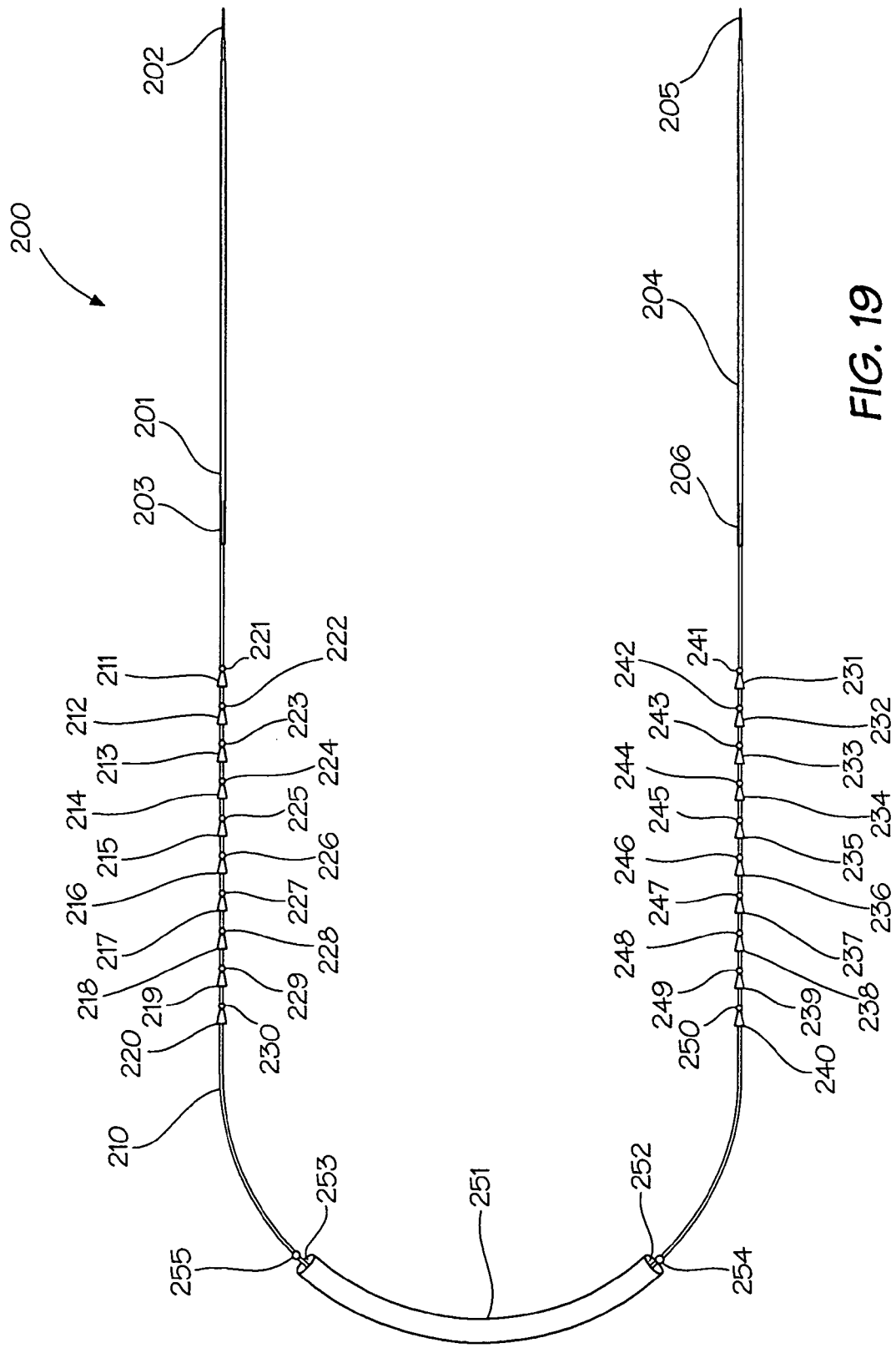
FIG. 19 sets forth a side view of a complete suture assembly constructed in accordance with the present invention supporting a porous tissue bonding sleeve.

FIG. 19 sets forth a side view of a complete suture structure constructed in accordance with an alternate embodiment of the present invention and generally referenced by numeral 200. By way of overview, suture assembly 200 is constructed generally in accordance with the fabrication of suture 10 set forth above in FIG. 1, in that it provides a pair of generally rigid needle-like structures joined by an elongated flexible body. In further similarity, it will be noted that suture assembly 200 includes a plurality of tissue engaging elements which are positioned upon the elongated flexible body by corresponding positioning elements such as knots or enlarged beads. Suture assembly 200 differs from the suture assembly set forth above in that it further includes an elongated portion of the flexible body which is free of the tissue engaging elements and which supports an elongated tissue bonding sleeve positioned upon the flexible body. As described below, the function of the tissue bonding sleeve is to provide a mechanism for further enhancing the gripping and tissue engaging characteristics of suture 200. In essence, the porous structure of the tissue bonding sleeve allows the growth of tissue into that porosity and strongly bonds the sleeve and as a result the suture to the patients tissue. The inventive suture may be fabricated using a variety of implantable materials including absorbative or non-absorbative materials.

More specifically, suture 200 includes a pair of elongated generally resilient needles 201 and 204 having respective sharp ends 202 and 205. Needles 201 and 204 further define respective attachment ends 203 and 206. An elongated flexible body 210 is secured between end attachments 203 and 206 of needles 201 and 204. It will be noted that in the example shown for suture 200 in FIG. 19, both needles 204 define straight needles. However, it will be apparent to those skilled in the art that either or both of needles 201 and 204 may define curved or hooked segments as shown above in FIG. 1.

In accordance with the fabrication set forth above, elongated flexible body 210 supports a plurality of spaced tissue engaging elements 201 through 220 which are positioned upon body 210 by a corresponding plurality of knots 221 through 230. Further, elongated flexible body 210 supports a second plurality of tissue engaging elements 231 through 240 which are positioned upon elongated flexible body 210 by a corresponding plurality of knots or other positioning elements 241 through 250. It will be apparent to those skilled in the art from the descriptions which follow that positioning elements 221 through 230 as well as positioning elements 241 through 250 may alternatively be knots tied in elongated flexible body 210 or may comprise headed or beaded segments in the manner set forth below and illustrated in FIG. 20.

In accordance with the alternate embodiment of the present invention, elongated flexible body 210 defines a portion which is free of tissue engaging elements 211 through 220 and 231 through 240. It is upon this portion of elongated flexible body 210 that elongated flexible tissue bonding sleeve 251 is supported. For purposes of illustration, sleeve 251 is shown supported upon body 210 generally equidistant from the two sets of tissue engaging elements thereon. It will be apparent however that the position of sleeve 251 may be varied in accordance with specific needs of suture 200. Sleeve 251 is positioned by positioning elements 254 and 255 at ends 252 and 253 respectively of sleeve 251.

In its preferred fabrication, sleeve 251 is elongated and some what flexible and defines a center passage allowing it to be supported upon elongated flexible body 210. In further accordance with the preferred fabrication of the present invention, sleeve 251 is preferably formed of a material such as gortex or other suitable implantable material. The preferred function of the sleeve 251 is realized as the generally porous structure of sleeve 251 allows the tissue within the patient to "grow into" or bond with the body of sleeve 251. This process provides an enhanced tissue gripping capability as the patients tissue extends into and bonds with the body of sleeve 251.

As mentioned above, the present invention suture may be fabricated utilizing a variety of differently shaped tissue engaging elements. Additionally, and as is also mentioned above, the attachment or positioning of these tissue engaging elements may be similarly varied upon the elongated flexible body portion of the suture. Thus, FIGS. 20 through 24 set forth below provide side views of portion of these alternate embodiment sutures which may be fabricated in accordance with the various embodiments of the present invention. Thus, in FIGS. 20 through 24 it will be understood that the Figures show a portion of the suture assembly which, in its entirety, is fabricated in the manner indicated in FIGS. 1 and 19 and in accordance with the construction shown therein for sutures 10 and 200.

Figure 20:
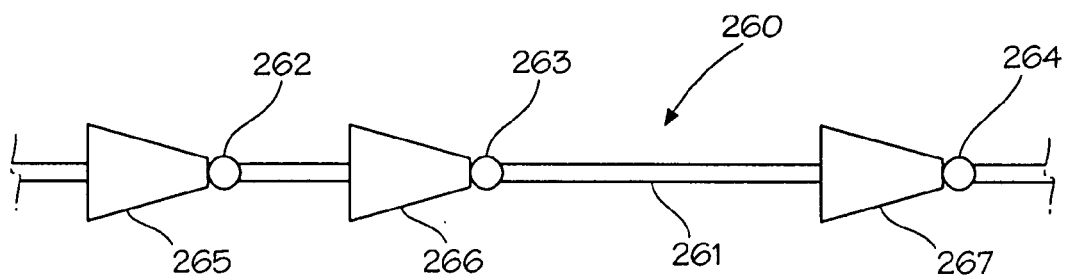
FIG. 20 sets forth a side view of a suture portion having tissue-gripping elements which are nonuniformly spaced.

More specifically, and with reference to FIG. 20, a suture portion 260 is shown having an elongated flexible body 261 within which a plurality of positioning elements 262, 263 and 264 are formed. Positioning elements 262, 263 and 264 may alternatively comprise knots tied in flexible body 261 or may be molded or headed onto the flexible body in the manner illustrated in FIG. 3. In a simple embodiment, the tissue engaging elements may be formed by simply "flattening" the flexible body to form enlargement thereof in one dimension. Body 261 supports a corresponding plurality of tissue engaging elements 265, 266 and 267. Of importance to note in FIG. 20 is the non uniform spacing of tissue engaging elements 265, 266 and 267. Thus, it will be apparent to those skilled in the art while in many instances uniform spacing of tissue engaging elements is contemplated and may be utilized, there remain other applications in which the spacing of tissue engaging elements may be varied and may be non uniform as desired.

Figure 21:
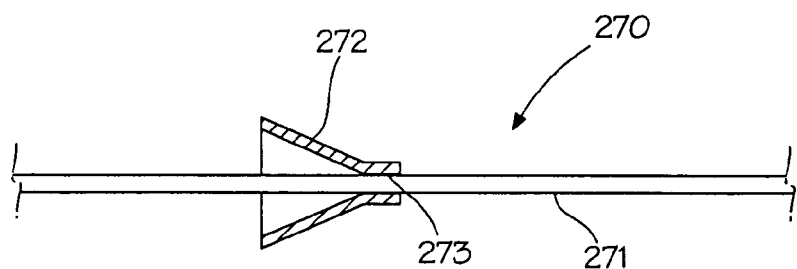
FIG. 21 sets forth a partial section side view of a suture portion constructed in accordance with the present invention having a tissue-gripping element secured to the elongated filament of the suture assembly by attachment utilizing laser welding, ultrasonic welding, or adhesive attachment.

FIG. 21 sets forth a suture portion 270 having an elongated flexible body 271 upon which a tissue engaging element 272 is supported. Of importance to note in FIG. 21 is the utilization of an attachment 273 between tissue engaging element 272 and body 271 which provides a direct attachment and which may avoid the need for positioning elements. This attachment may, for example, comprise ultrasonic welding, laser welding, adhesive attachment or other direct attachment mechanisms.

Figure 22:
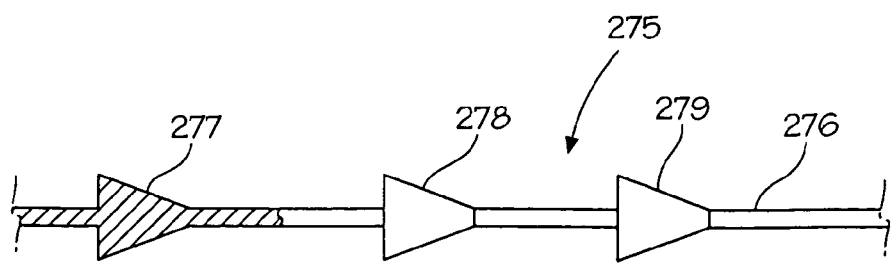
FIG. 22 sets forth a partial section side view of a suture portion constructed in accordance with the present invention having a plurality of tissue-gripping elements formed by molding or heading process.

FIG. 22 sets forth a partially sectioned side view of a suture portion 275. The importance of suture portion 275 is its utilization of a one piece structure for the flexible body and tissue engaging elements. Thus, flexible body 276 is molded or headed to provide a plurality of tissue engaging elements 277, 278 and 279. Such molding or heading processes are known in the art and may be utilized in some embodiments of the present invention.

Figure 23:
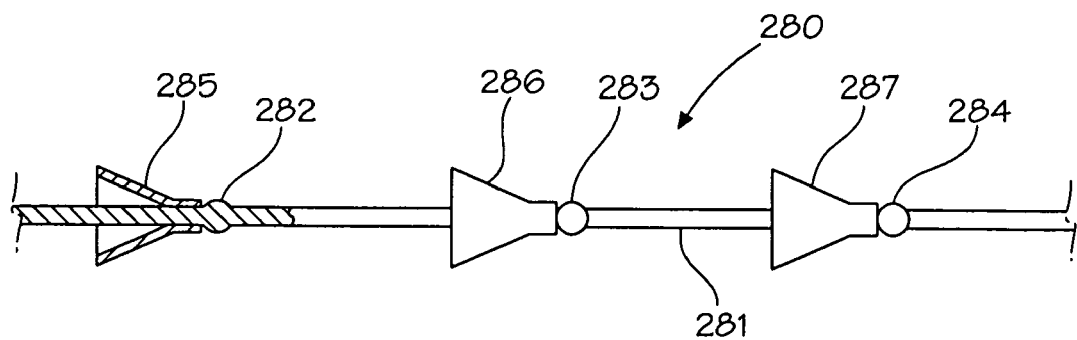
FIG. 23 sets forth a partial section side view of a suture portion constructed in accordance with the present invention having a plurality of tissue engaging elements positioned by a plurality of integrally formed enlargements on the filament body.

FIG. 23 sets forth a partial section side view of a suture portion 280 having an elongated flexible body 281 within which a plurality of positioning elements 282, 283 and 284 are formed as an integral portion of body 281. This integral formation may be provided by heading or molding processes or staking or impacting processes. With positing elements 282, 283 and 284 as shown, a corresponding plurality of tissue engaging elements 285, 286 and 287 are positioned upon body 281.

Figure 24:
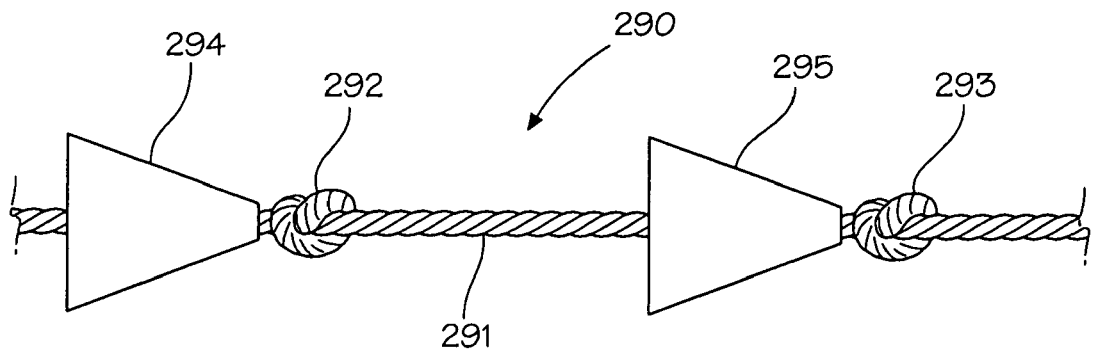
FIG. 24 sets forth a side view of a suture portion constructed in accordance with the present invention utilizing a braided or woven multi strand filament.

FIG. 24 sets forth a side view of a suture portion generally referenced by numeral 290 which utilizes a multi strand braided or woven elongated flexible body 291. Body 291 may be fabricated of a variety of implantable materials such as braided polyester, nylon or other materials. A plurality of positioning elements 292 and 293 are formed in body 291 as tied knots therein. A corresponding plurality of tissue engaging elements 294 and 295 are also shown upon body 291. Of importance with respect to the embodiment of the present invention shown in FIG. 24, the braided or woven character of body 291 further enhances the tissue bonding characteristic of the entire suture structure. The braided or woven characteristic of body 291 allows tissue growth to adhere to and grow into the spacing between the various braided or woven strands of body 291. In this manner, the tissue adherence is greatly enhanced as the entire flexible body of the suture assembly provides direct tissue bonding superior to that realized with the single filament flexible bodies used in sutures. The braided or woven character of body 291 provides better attachment or tissue bonding initially. But perhaps of more importance is the eventual growth into the spaces within the braided or woven strands which provides tissue engagement along the entire length of the flexible body portion of the suture.

What has been shown is a novel suture assembly which provides an implantable directional camming device which maybe either directional or bi-directional in fabrication. The suture assembly shown may be fabricated using injection molded or cold-headed manufacturing techniques and is suitable for use in wound closure, tissue approximation, tissue support, suspension and/or fixation. Tissue engaging elements are shown which provide either circular cross-section or elliptical cross-section. The present invention suture assembly may be inserted into the human body either with or without the use of an introducer. The present invention suture is designed to work in conjunction with the healing process post surgical. The inventive suture assembly shown holds wounds closed without the need for suture knot tying to maintain tissue approximation.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A suture assembly for use in cosmetic surgery, aesthetic surgery, and soft tissue fixation, said suture assembly comprising:

a singular, uninterrupted, flexible, elongate polymeric suture thread having a first and second ends, and a plurality of knots formed in and spaced along said suture thread; and a plurality of tissue-engaging elements for anchoring said suture assembly on subcutaneous tissues, said tissue-engaging elements comprising a hollow frustoconical shape, each tissue-engaging elements defining an enlarged hollow interior having a tapered lumen including a forward bore at a narrow end of the tapered lumen and enlarging outwardly toward a broader end of the tapered lumen;

wherein each tissue-engaging element is received upon said suture thread through the forward bore of said tissue-engaging element and between each knot on said suture thread for providing a serial arrangement on said suture thread and fitted for one of: restricted movement and direct attachment, and wherein each knot is larger than said forward bore for securing said tissue-engaging elements on said suture thread.

2. The suture assembly of claim 1, further comprising a curved end having a sharp-pointed end and a connector end joined to the first end of said suture thread; and an elongate body having a pointed end and a connector end joined to said second end of said suture thread.

3. The suture assembly of claim 1, wherein said tissue-engaging elements define generally circular cross sections.

4. The suture assembly of claim 1, wherein said tissue-engaging elements define generally elliptical cross-sections.

5. The suture assembly of claim 1, wherein said suture thread measures at least about 12 centimeters between each end, said plurality of knots includes about two to forty knots, and the distance between each knot is about one centimeter.

6. The suture assembly of claim 1, wherein an outer surface of said tissue-engaging elements comprises a plurality of facets.

7. The suture assembly of claim 1, wherein said suture thread is formed from a material selected from the class consisting of polyester, nylon, polypropylene, polyolefin, absorbable materials, PDF and gortex.

8. The suture assembly of claim 7, wherein the suture thread is braided.

9. The suture assembly of claim 1, wherein the suture thread is braided.

10. The suture assembly of claim 1, wherein a spacing of the tissue-engaging elements on said suture thread is non-uniform.

11. The suture assembly of claim 1, further comprising a sleeve supported on the suture thread, thereby forming a bond with said subcutaneous tissue.

12. The suture assembly of claim 11, wherein the sleeve is constructed of gortex.

13. The suture assembly of claim 1, wherein the tissue-engaging members are oriented in a bidirectional manner along the suture thread.

* * * * *